US011684921B1

(12) United States Patent
Betts et al.

(10) Patent No.: US 11,684,921 B1
(45) Date of Patent: Jun. 27, 2023

(54) POCKET DETECTION POUCH

(71) Applicants: Leidos, Inc., Reston, VA (US); Jennifer W. Sekowski, Forest Hill, MD (US)

(72) Inventors: Kelley D. Betts, Rising Sun, MD (US); Jennifer W. Sekowski, Forest Hill, MD (US)

(73) Assignees: Leidos, Inc., Reston, VA (US); The United States of America as Represented by the Secretary of the Army, Washington, DC (US)

( * ) Notice: Subject to any disclaimer, the term of this patent is extended or adjusted under 35 U.S.C. 154(b) by 336 days.

(21) Appl. No.: 16/988,368

(22) Filed: Aug. 7, 2020

Related U.S. Application Data (60) Provisional application No. 62/888,134, filed on Aug. 16, 2019.

(51) Int. Cl.
| | | |
|---|---|---|
| *B01L 3/00* | (2006.01) | |
| *G01N 33/53* | (2006.01) | |
| *G01N 1/02* | (2006.01) | |

(52) U.S. Cl.
CPC .......... *B01L 3/502715* (2013.01); *G01N 1/02* (2013.01); *G01N 33/5302* (2013.01);
(Continued)

(58) Field of Classification Search
CPC ........ B01L 3/00; B01L 3/50; B01L 3/502715; B01L 2200/027; B01L 2200/0689;
(Continued)

(56) References Cited

U.S. PATENT DOCUMENTS

| | | | | |
|---|---|---|---|---|
| 5,084,041 A | * | 1/1992 | Oxley ..................... | B01L 3/505 604/408 |
| 7,227,158 B1 | * | 6/2007 | Patel ........................ | G01T 1/04 250/484.5 |

(Continued)

FOREIGN PATENT DOCUMENTS

| | | | |
|---|---|---|---|
| CN | 102338799 A | * | 2/2012 |
| CN | 205891583 U | * | 1/2017 |

(Continued)

OTHER PUBLICATIONS

Gao et al., Translation of CN-102338799-A, 2012, Espacenet, 8 pages (Year: 2012).*
Jiang, Translation of CN-205891583-U, 2017, Espacenet, 3 pages (Year: 2017).*
Jody Gostomski, et al., "Biological Environmental Sampling Technologies Assessment," Edgewood Chemical Biological Center, U.S. Army Research, Development and Engineering Command, Aberdeen Proving Ground, MD 21010-5424, ECBC-TR-1327, 58 pp., Dec. 2015.

*Primary Examiner* — Bao-Thuy L Nguyen
*Assistant Examiner* — Jennifer H. Tieu
(74) *Attorney, Agent, or Firm* — Dawn-Marie Bey; Bey & Cotropia PLLC (57) ABSTRACT

The pocket detection platform (PDP) detects pathogens, toxins and chemicals of interest simultaneously by way of a multi-channeled, soft see-through plastic pouch design that consists of inner and outer compartments that promote compartmentalization and/or unidirectional sample flow. The platform enables the concurrent running of multiple detection assay techniques such as lateral flow immunoassays (LFI), Isothermal molecular assays (i.e., Recombinase Polymerase Amplification, or RPA) and/or paper-based chemical assays (i.e., M8, pH paper) from a single wet or dry sample with minimal sample processing. The PDP reduces soldier overburden by decreasing size weight, and power (SWaP) as well as training time, electronic burden, while providing a flexible, customizable assay platform that can be rapidly produced, assembled, sustained, and when contaminated, easily to dispose of.

14 Claims, 7 Drawing Sheets

(52) U.S. Cl.
CPC . *B01L 2200/027* (2013.01); *B01L 2200/0689* (2013.01); *B01L 2200/10* (2013.01); *B01L 2300/04* (2013.01); *B01L 2300/0636* (2013.01); *B01L 2300/0809* (2013.01); *B01L 2300/123* (2013.01); *B01L 2300/126* (2013.01); *G01N 2001/028* (2013.01)

(58) Field of Classification Search
CPC ............ B01L 2200/10; B01L 2300/04; B01L 2300/0636; B01L 2300/0809; B01L 2300/123; B01L 2300/126; B01L 3/502; G01N 1/00; G01N 1/02; G01N 33/00; G01N 33/50; G01N 33/53; G01N 33/5302; G01N 2001/028
See application file for complete search history.

(56) References Cited

U.S. PATENT DOCUMENTS

2011/0144535 A1* 6/2011 Guirguis ............ A61B 10/0038
                                                          600/573
2017/0307605 A1* 10/2017 Hudson ................ G01N 33/558

FOREIGN PATENT DOCUMENTS

| WO | WO-9015328 A1 * | 12/1990 | |
|----|---|---|---|
| WO | WO-2005073721 A1 * | 8/2005 | ....... G01N 33/56955 |
| WO | WO-2018022971 A1 * | 2/2018 | ........ B01L 3/502738 |

* cited by examiner

Sample Flow →

| | Positive | Negative |
|---|---|---|
| 1 | Bacterial Agent #1 | B1 |
| 2 | Bacterial Agent #2 | B2 |
| 3 | Bacterial Agent #3 | V1 |
| 4 | Viral Agent #1 | V2 |
| 5 | Biological toxin | TX |

Sample Input →

POCKET DETECTION POUCH

CROSS-REFERENCE TO RELATED APPLICATION

The present application claims benefit of priority to U.S. Provisional Patent Application No. 62/888,134, entitled "Pocket Detection Pouch," filed Aug. 16, 2019, the entirety of which is incorporated herein by reference.

GOVERNMENT RIGHTS

This invention was made with government support under the U.S. Army Combat Capabilities Development Command (CCDC) Chemical Biological Center (CBC) Innovative Development of Advanced Employee Solutions (IDEAS) Program in 2019. The government has certain rights in the invention.

BACKGROUND

Technical Field of the Embodiments

A field-forward, self-contained, power-free, minimal size, weight, and power (SWaP) platform designed for liquid and powdered chemical, drug, biological, toxin, radiation, and explosives (CBRNe) collection/ detection.

Description of Related Art

For warfighters and first responders operating in potentially hazardous, field-forward and austere environments, the rapid and accurate detection of a Chemical, Biological, Radiological, Nuclear, and Explosive (CBRNE) threat is critical. There is a need in the art for a new form factor designed to provide power-free, field-forward, colorimetric presumptive identification of chemical and biological threat agents in the field that capable of interrogating a single sample simultaneously for multiple threats. An ideal device would be an inexpensive, customizable, simple-to-use assay form factor that requires no external power source, no specialized equipment, no cold chain logistics, and no proprietary software, all in a format about the size of a credit card that can be carried in a pocket. The device would be a self-contained assay platform with minimal size, weight and power (SWaP) designed for both liquid and powdered CBRNe collection and detection. The device would leverage current and up-and-coming commercial off-the-shelf (COTS) and Government off-the-shelf (GOTS) assay technologies to deliver simultaneous, eye-readable yes/no answers for multiple CBRNe targets rapidly or in less than an hour. The device would also contain a sample reservoir for later confirmatory laboratory-based testing such as culturing, genetic sequencing, or chemical testing, should they be needed.

The PDP design accommodates paper-based detection technologies, lateral flow immunoassays (LFIs), and isothermal DNA amplification assays to provide tiered, orthogonal identification and verification of chemical and biological agents. The current design of the PDP supports from 5-10 immuno-based assays (LFIs), but more highly multiplexed versions are possible. Nucleic acid-based identification using methods such as commercially available recombinase polymerase amplification (RPA) assay using an LFI-format readout could also be used in the PDP, requiring one lane per bioagent-specific assay. Rapid, antigen-specific LFI assays provide yes/no answers within 10 minutes, while an additional orthogonal isothermal DNA-amplification assay, such as one provided by a COTS RPA molecular assay, would yield an LFI-style "yes/no" readout in 20 min to 2 hours (temperature dependent).

Molecular detection methods like polymerase chain reaction (PCR), loop-mediate isothermal amplification (LAMP), and RPA, currently require a power source, cold chain storage, and reliance on specialized equipment such as a thermos-cycling apparatus, and data visualization tools, making most molecular pathogen detection methods impractical or burdensome in austere or resource-poor environments. Many of these platforms generally have a limited, non-transferable license for use which tend to be reliant on periodic updates. The ability to bring molecular detection capabilities to the field that eliminate the need for power, equipment and software would be a game-changer in today's filed detection capability, and was the inspiration behind the design of the PDP.

SUMMARY OF CERTAIN EMBODIMENTS

In a first embodiment, a pocket-sized detection device for detection of one or more analytes, the device includes: a first sample compartment for receiving a sample which may contain the one or more analytes, the first sample compartment including a first sealing component for sealing the first sample compartment once the sample has been received therein; a second compartment in fluid connection with the first sample compartment for receiving a fluid sample therefrom, the second compartment containing multiple individual channels; a third compartment, including a reservoir, for (i) loading therethrough individual detectors for placement in the individual channels; and (ii) receiving at least some of the sample fluid therein from the second compartment, the third compartment including a second sealing component for sealing the third compartment once the individual detectors are loaded in the individual channels; wherein, once the first and second sealing components are sealed, the pocket-sized device retains the fluid sample therein.

In a second embodiment, a pocket-sized detection device including multiple individual detectors for detecting multiple different analytes of interest, includes: a fully enclosable system having multiple compartments, including an internal compartment which includes multiple independent channels for receiving a liquid sample, wherein each independent channel directs a portion of the liquid sample to a specific detector associated with the independent channel and enclosed within the fully enclosable system for detecting multiple different analytes of interest; and wherein the fully enclosable system is formed from at least one of the following materials selected from the group consisting of polyethylene low density (LDPE) plastic, polypropylene film or poly nylon plastic.

In a third embodiment, a system for field collection and testing of substances for analytes of interest from one or more surfaces, includes: a collector for collecting a sample from a surface; a port for connecting the collector to a pocket-sized detection device for facilitating transfer of the sample from, wherein the pocket-sized detection devices includes a fully enclosable system having multiple compartments, including an internal compartment which includes multiple independent channels for receiving a liquid sample, wherein each independent channel directs a portion of the liquid sample to a specific detector associated with the independent channel and enclosed within the fully enclosable system for detecting multiple different analytes of interest; and wherein the fully enclosable system is formed from at least one of the following materials selected from the group consisting of polyethylene low density (LDPE) plastic, polypropylene film or poly nylon plastic.

BRIEF DESCRIPTION OF FIGURES

In addition to the figures found in the materials incorporated herein by reference, the present patent or application file contains at least one drawing executed in color. Copies of this patent or patent application publication with color drawing(s) will be provided by the Office upon request and payment of the necessary fee.

DETAILED DESCRIPTION

As described herein with respect to the figures, a "Pocket Detection Pouch" (PDP) is a low burden, lightweight, eye-readable point collection/detection and power-free assay platform that can be customized to detect pathogens, toxins, chemicals, PBAs and pharmaceutical-based agents of interest from a single sample. The PDP described herein delivers accurate, sample-to-results of multiple CB targets simultaneously in less than 20 minutes. The platform is an inexpensive, multi-channeled plastic pouch with an inner compartment that promotes compartmentalization and/or unidirectional sample flow and is designed to perform multiple detection assays simultaneously from a single liquid or wetted solid sample. It can simultaneously and from a single sample accommodate a variety of detection assays such as lateral flow immunoassays (LFIs), isothermal DNA amplification /detection techniques, loop-mediate isothermal amplification (LAMP) nucleic acid assays, and chemical reactive papers (e.g., M8 paper), all of which yield rapid, eye-readable "yes/no" answers. The PDP is designed to think "outside the tube" to deliver an inexpensive, customizable, simple-to-use assay form factor that requires no external power source, specialized equipment, cold chain logistics, or proprietary software—in a format about the size of a credit card.

Figure 1A:
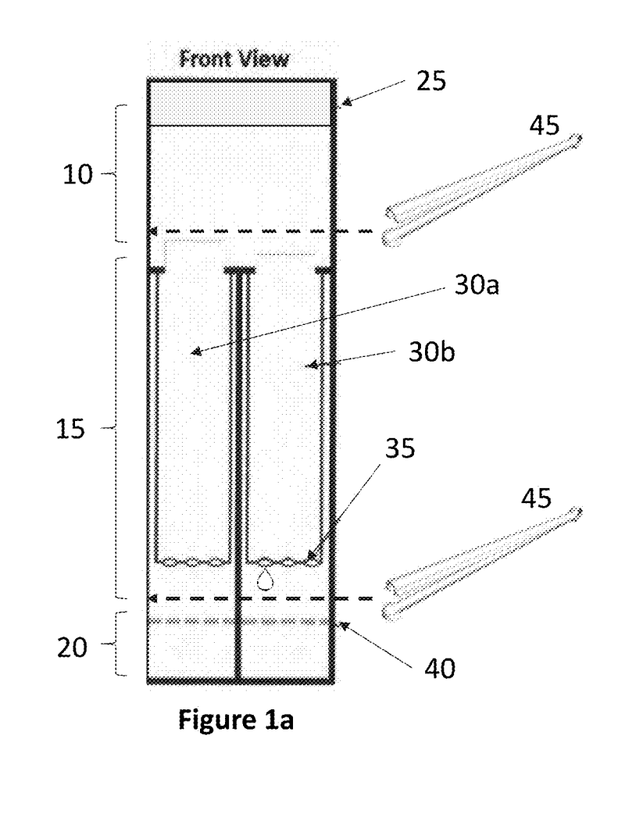
FIGS. 1a, 1b and 1c show a first exemplary embodiment of a Pocket Detection Pouch (PDP) platforms in accordance with one or more embodiments described herein.
Figure 1B:
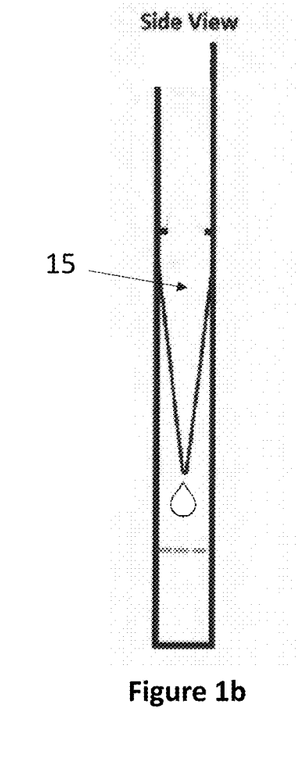
Figure 1C:
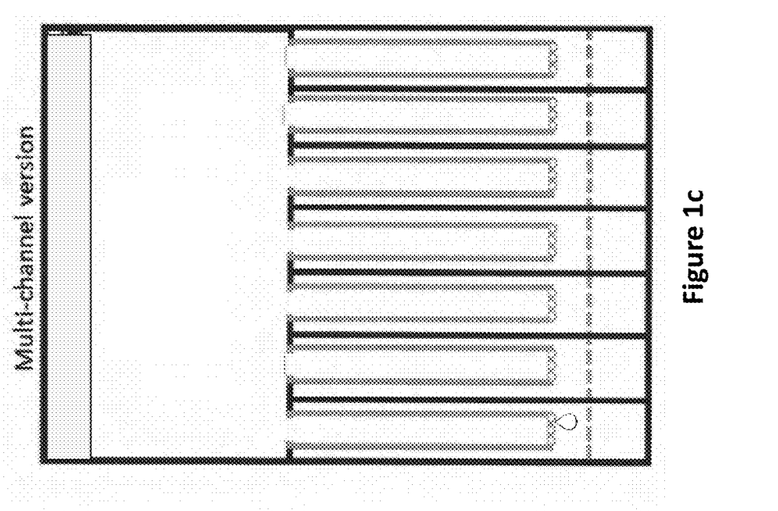

FIGS. 1a-1c show front (FIGS. 1a, 1c) and side (FIG. 1b) views of a first exemplary PDP platforms. FIGS. 1a and 1c differ only in the number of channels. All embodiments of the exemplary PDP platforms include three primary sections: sample compartment 10, continue into an inner bag or bladder 15 with individual channels $30_{a-x}$, and reservoir 20. Additionally, each individual channel $30_{a-x}$ includes micropores (or perforations) 35 at ends thereof closest to the reservoir 20. FIGS. 1a-1c include a flap closure 25 (alternatively, this could be a zip closure), a fill line 40 and components may be sealed off from one another using sealing clips 45. FIG. 1c illustrates a multi-channel version of the FIG. 1a. In FIG. 1b, which is a side view of the PDP platform in accordance with the embodiments herein, the inner bag can be seen 15.

Figure 2A:
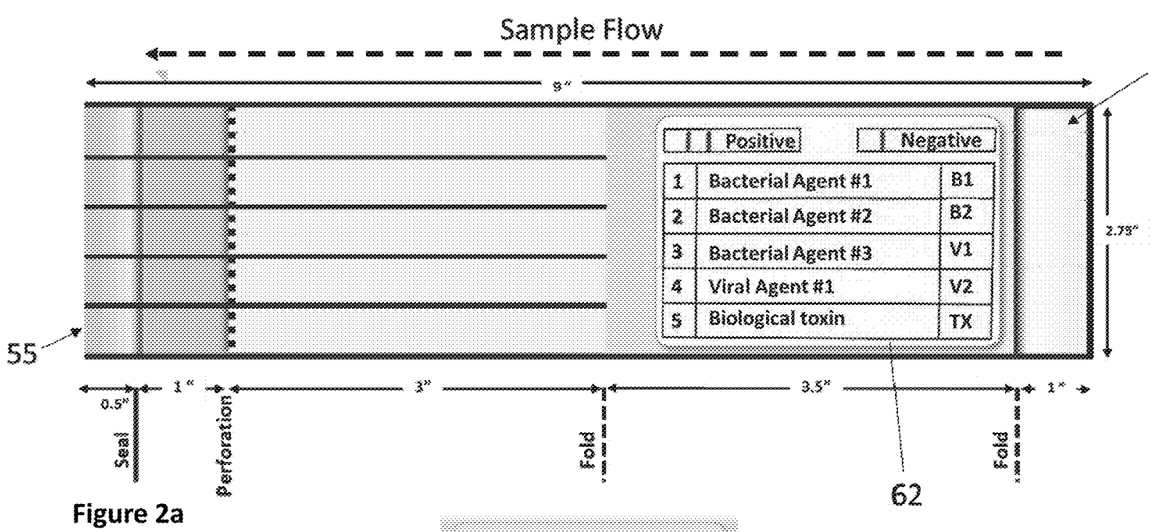
FIGS. 2a, 2b and 2c show a second exemplary embodiment of a PDP platform in accordance with one or more embodiments described herein.
Figure 2B:
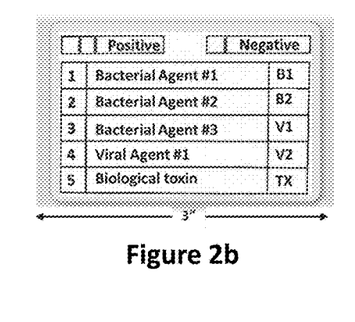
Figure 2C:
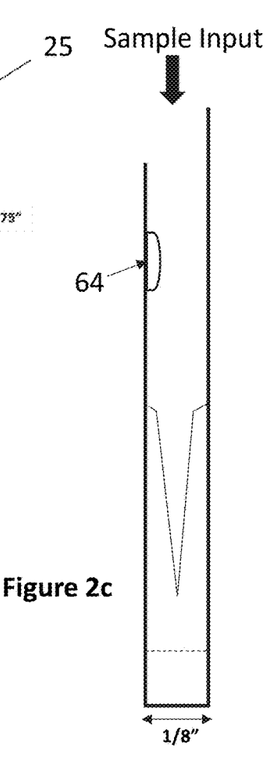

FIGS. 2a through 2c show a second exemplary embodiment of the PDP platform. The second exemplary embodiment has an open configuration (FIG. 2a) and folded configuration (FIG. 2b). In addition to the primary sections described above and illustrated with respect to FIGS. 1a-1c, the second embodiment includes the flap closure 25 which may be formed with double sided adhesive tape (e.g., approximately 0.25 to 1 inch width) and a loading flap 55 which is used to load the individual detectors into individual channels and is then heat sealed or, if loaded in the field by the user, sealed with a second flap of double sided adhesive tape. The loading flap 55 includes an adhesive edge which may be used to seal and close off a reservoir and channel access end of the PDP platform when not in use. One skilled in the art recognizes that such adhesive flaps, edges/surfaces are well known and may be implemented such that a removable or tear away tabs are used to cover the adhesive edge/surface until read for use.

A reference key card 62 to compare to the assay results from the individual channels 1 to 5 is held in the primary compartment prior to use and is removed before the sample is added therein. Further, as referenced below, one or more blister pouches 64 containing a buffer or other liquid could be formed within the sample compartment 10 and popped by the user, if needed, to release the buffer and mix with the sample. The PDP dimensions referenced in FIGS. 2a and 2b are exemplary and approximate and variations are expected and included while still meeting the requirements for making the PDP hand-held.

Figure 3A:
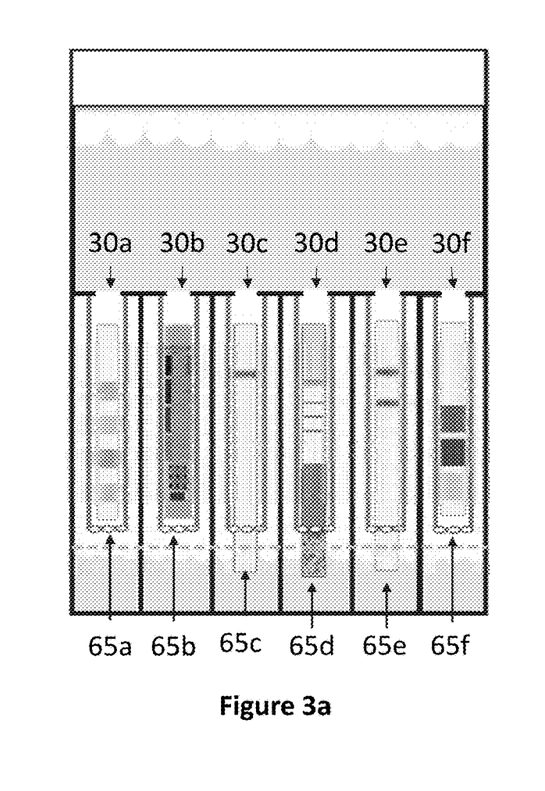
FIGS. 3a, 3b, 3c, 3d show an exemplary PDP platform including detectors and detector arrangements within the PDP.

FIGS. 3a to 3d provide exemplary front and side views of a PDP platform showing different configurations for the location of the individual detectors within the platform. In FIG. 3a, there are six channels, 30a, 30b, 30c, 30d, 30e, 30f loaded with different types of detectors, including assay tickets or strips 65a-65f. The detectors are loaded into the individual, separate channels by, e.g., a shoe horn loading tool, at the reservoir 20 end of the PDP platform through a loading flap 55.

Figure 3B:
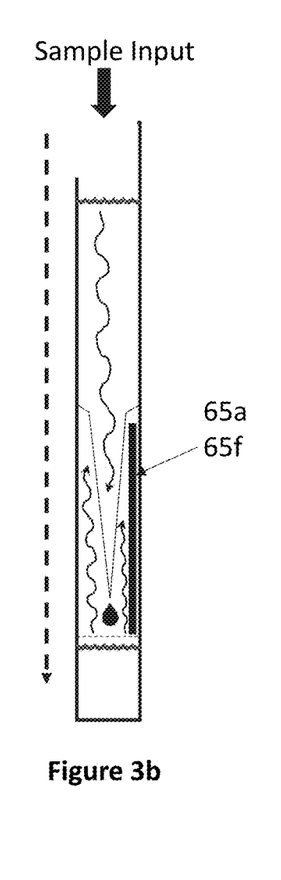
Figure 3C:
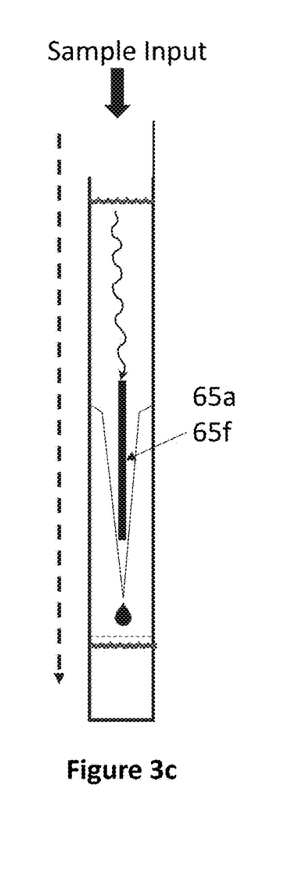
Figure 3D:
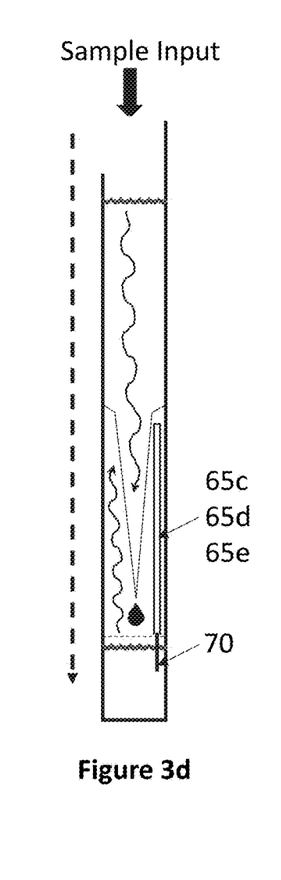

In the specific example shown in FIG. 3a, channels 30a and 30f user paper-based assays, channels 30c, 30d and 30e use wick-based assays and channel 30b uses a radiation detector. Depending on the type of detector, the sample may need to wash over the assay, as in the case of a paper-based assay, e.g., M8 and pH (65a, 65f), as shown in FIGS. 3b and 3c; the sample may need to encounter a wick 70, as is the case with traditional immuno-based LFI's and LFI-based isothermal molecular assays, biological and PBA lateral flow assays (65c, 65d, 65e) as shown in FIG. 3d. In the case of an always-on radiation detector (65b), the sample does not need to interact with the detector as general proximity of a radiating sample to the detector should register. Alternatively, the radiation detector (65b) could also be included in the primary component as a separate device or as part of the reference key card 62 as this proximity detector does not require direct physical contact with the sample. Many detectors exist as commercial-off-the-shelf or Government-off-the-shelf strips which are usable as-is or slightly modified in the individual PDP channels. The 6-channel PDP of FIG. 3a covers the spectrum of CBRNE detection including, e.g., chemical 65a, PBA (opioids, etc.) 65b, biological—DNA (e.g., bacteria, virus, toxin) 65c, biological—antibody (e.g., bacteria, virus, toxin) 65d, radiation (RAD Triage 50® Sensor, etc.) 65e, and pH/Explosives 65f. Further, some detectors are able to detect multiple agents on a single strip.

Further, some detectors may be able to detect multiple agents on a single strip by displaying their positive colorized results in the form of letters or symbols for the individual substances, potentially negating the need for a key card in some embodiments or allowing for the multiplexing of testing on a single strip.

Figure 4A:
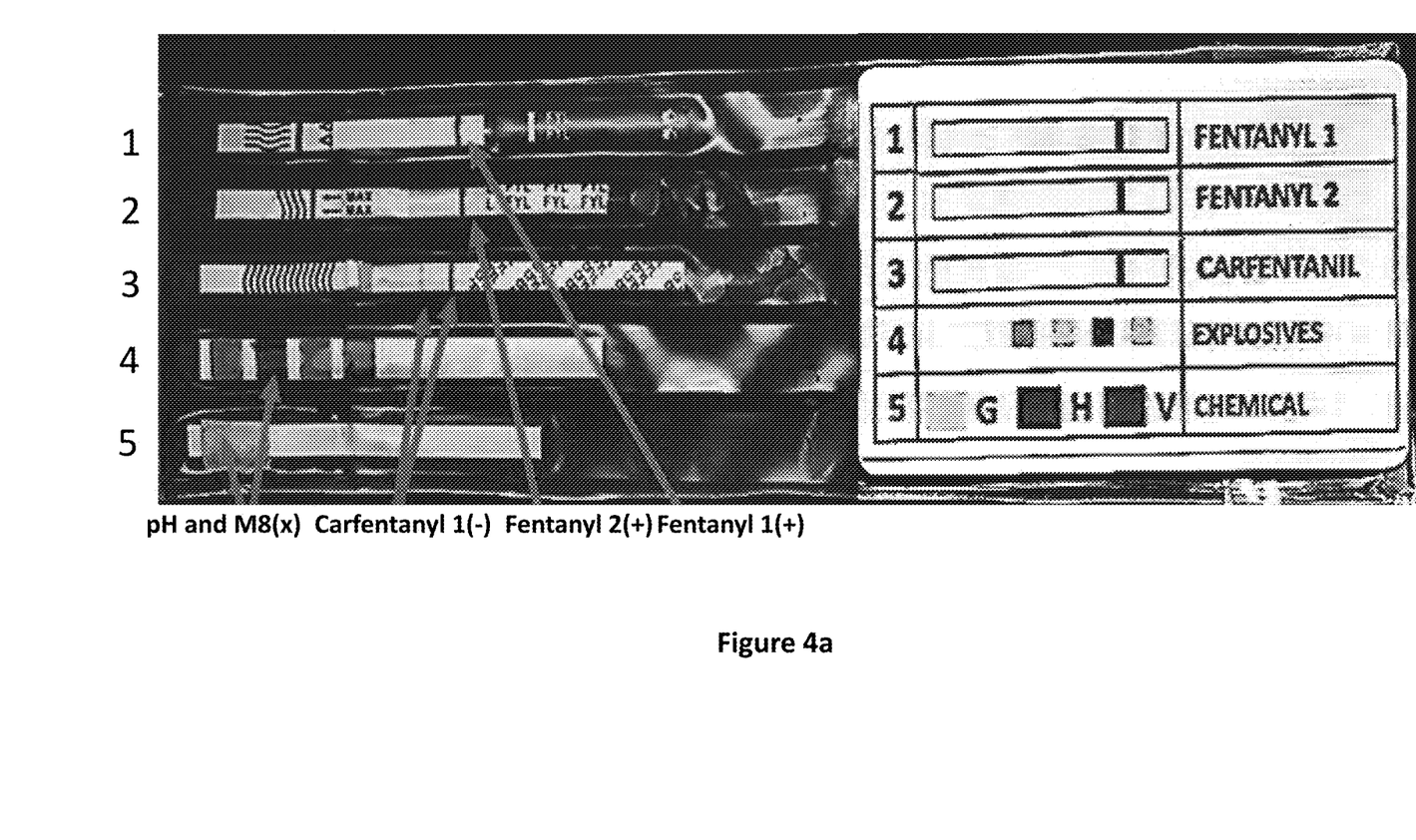
FIGS. 4a and 4b show exemplary PDP platforms post-use.
Figure 4B:
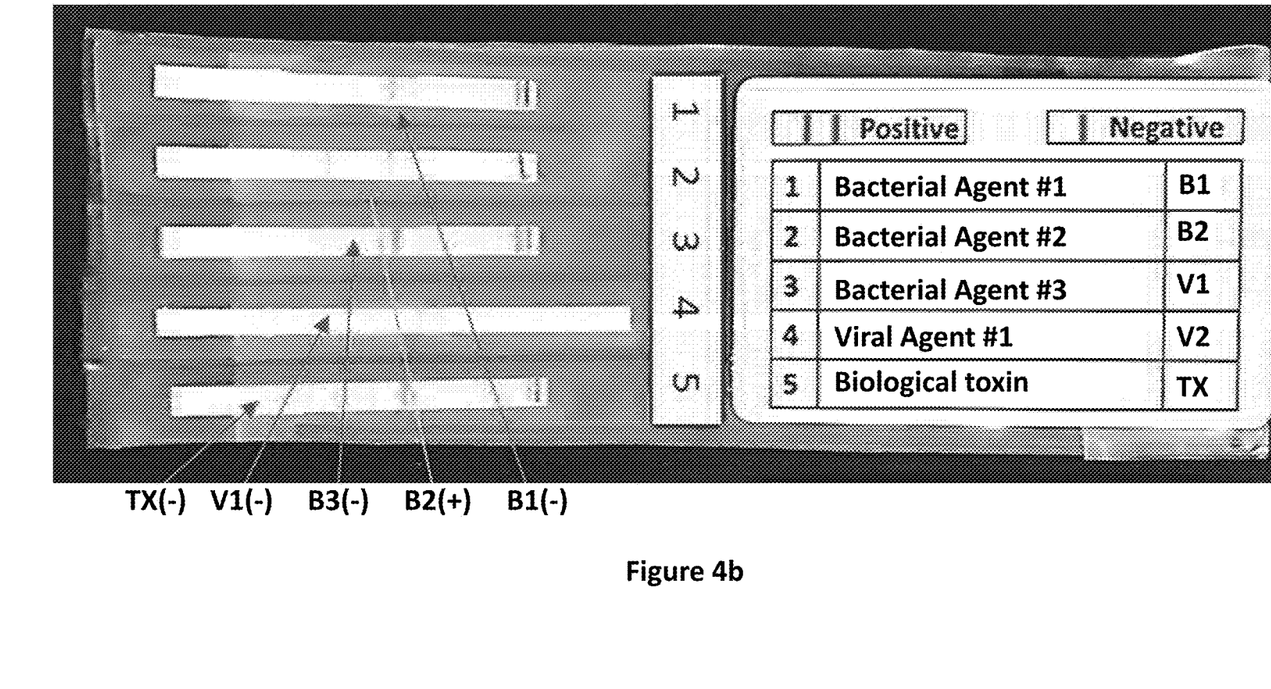

FIGS. 4a and 4b are examples of PDP platforms showing results for particular detectors post-use and including the reference key card for the associated detectors in the corresponding slots 1 through 5. In FIG. 4a, the assay detectors included three LFI assay detectors and two paper-based assay detectors. Specifically, channel 1 is an LFI for detecting fentanyl (such as the assay sold by BTNX); channel 2 is an commercially available LFI for detecting fentanyl; channel 3 is an commercially available LFI for detecting carfentanyl; channel 4 is pH paper for explosives detection and channel 5 is M8 paper for chemical agent detection. As indicated, both of the fentanyl detectors returned positive results, the carfentanyl was negative and the results were negative for explosives and chemical agents.

In FIG. 4b, the assay detectors are LFI immunoassay detectors for detecting certain biological agents, including bacteria and biological toxins. Specifically, channel 1 detects presence of bacterial agent #1; channel 2 detects presence of bacterial agent #2; channel 3 detects presence of bacterial agent #3; channel 4 detects presence of viral agent #1 and channel 5 detects presence of a biological toxin. As indicated, only channel 2 returned a positive result for bacterial agent #2.

Figure 5:
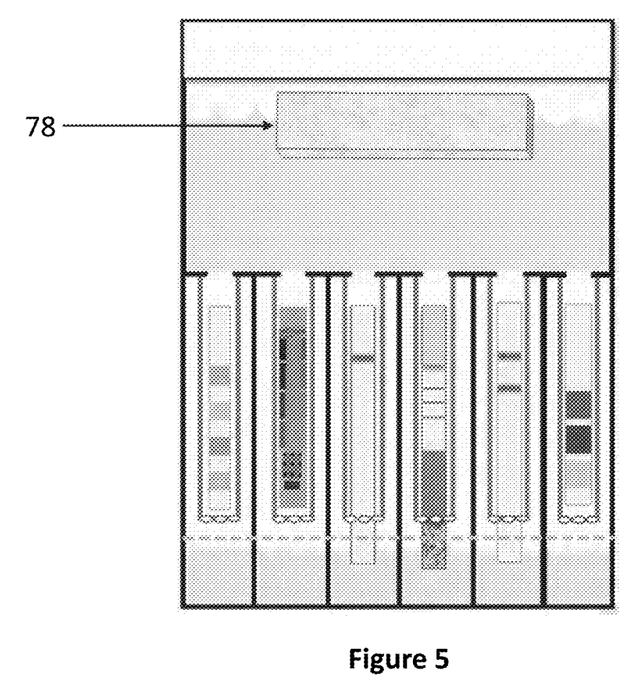
FIG. 5 shows a PDP platform in accordance with one or more embodiments described herein.

In operation, the PDP's broad compatibilty with different collection modalities makes it capable of addressing a wide range of military and civilian field-forward environments including detection of suspicious powders or liquids in the field, swipe scanning of packages, and food safety monitoring. In a first collection modality, the same is collected directly into the PDP using a sponge, swab, or pipette. FIG. 5 shows an exemplary PDP wherein a single-use sponge 78 is adhered to the inside of the sampling compartment and can be used by gently folding out the inside surface of the sampling compartment to access the sponge 78 to swipe a surface of interest.

Upon entering a suspected biothreat contaminated site, the PDP is opened at the sample end and a single suspected sample (solid or liquid) is placed (or swiped by the sponge) within the sample side of the upper primary compartment 10. Water or buffer is then added (directly or using an integrated blister pouch 64) and the sealing mechanism at the opening of the primary compartment 10 is closed. As shown in FIG. 1a, a sealing clip may be used between the primary compartment 10 and the inner bag or bladder 15 while the mixture is agitated by the tester using their fingers to help further disrupt any of the sample cells (if needed). Also, as needed, the primary compartment 10 could also contain a cell-lysing matrix (i.e. glass or garnet beads) for the disruption of cell walls in order to release nucleic acid from microbiological samples.

After mixing, the sealing clip, if used, is removed and the resulting mixed liquid sample is then pushed through the individual channels $30_{a-x}$ (also referenced as 1 to 5 in some embodiments) of the inner bag 15 and into the reservoir 20 where it eventually contacts the detectors, e.g, the wicking end of the LFIs, and/or washes over paper-based assays. Depending on the application, at the bottom of the internal bladder there may be micro-pores 35 that aid in separating the larger particulates of the sample (such as lysing beads, soil, etc.,) from the liquid mixture sample prior to the sample entering the final assay compartment or reservoir 20. Each individual channel $30_{a-x}$ (also referenced as 1 to 5 in some embodiments) is designed to allow only a limited amount of fluid into each assay reaction compartment (fill line) so that each assay occurs in the appropriate reaction volume. The size of the pores and the length of the lane significantly reduce the likelihood that fluid from one individual assay compartment will flow back and contaminate other assay compartments. Depending on the assay being performed, a colorimetric change will occur in less than 10 minutes to give eye readable "yes/no" results.

For specialized assays, such as LAMP, the assay bag can be re-clamped by a sealing clip at the bottom of the individual channels $30_{a-x}$ of the inner bag 15 (just above the fill line) prior to application of heat, which can be applied by sandwiching the assay bag between two disposable hand warmers. For molecular assays such as LAMP, the internal bladders feed the liquid into the PDP's bottom reservoir 20 that holds an individual assay against a unique target or an assay control.

For specialized assays, such as LAMP, the assay bag can be re-clamped by a sealing clip at the bottom of the individual channels $30_{a-x}$ of the inner bag 15 (just above the fill line) prior to application of heat (if required), which can be applied by sandwiching the assay bag between two disposable hand warmers. For molecular assays such as LAMP or RPA, the internal bladders feed the liquid into the PDP's bottom reservoir 20 that holds an individual assay against a unique target or an assay control.

The PDP can be customized by adding (or removing) lanes to the design, or by adjusting the sample compartment and the assay compartments sizes to adjust for assay volume requirements. The PDP platform is generally comprised of an inexpensive, readily-available plastic such as Polyethylene low density (LDPE), polypropylene film or poly nylon plastic. The individual channels and edges may be formed using a thermosealer or similar device. The design is customizable, cheap to produce; amenable to multiplexing; capable of testing small samples; and requires a negligible amount of sample processing. The PDP has the potential to reduce costs of biological detection assays in the field by ten-fold due to its use of inexpensive non-proprietary materials and low sustainment costs. Although by no means limiting, an exemplary embodiment of a PDP inlcudes the following specifications: pocket-sized, clear, flat 6 mil thickness polyurethane bag that is less than 4 inches by 3 inches (folded) and weighs less than 1 ounce. The internal bag 15 may be thinner, e.g., 2 to 4 mil thickness.

Additionally, since the PDP is an enclosed, self-contained system once sealed, the PDP preserves the sample for later testing and/or confirmation of field results in a laboratory or other setting.

Figure 6:
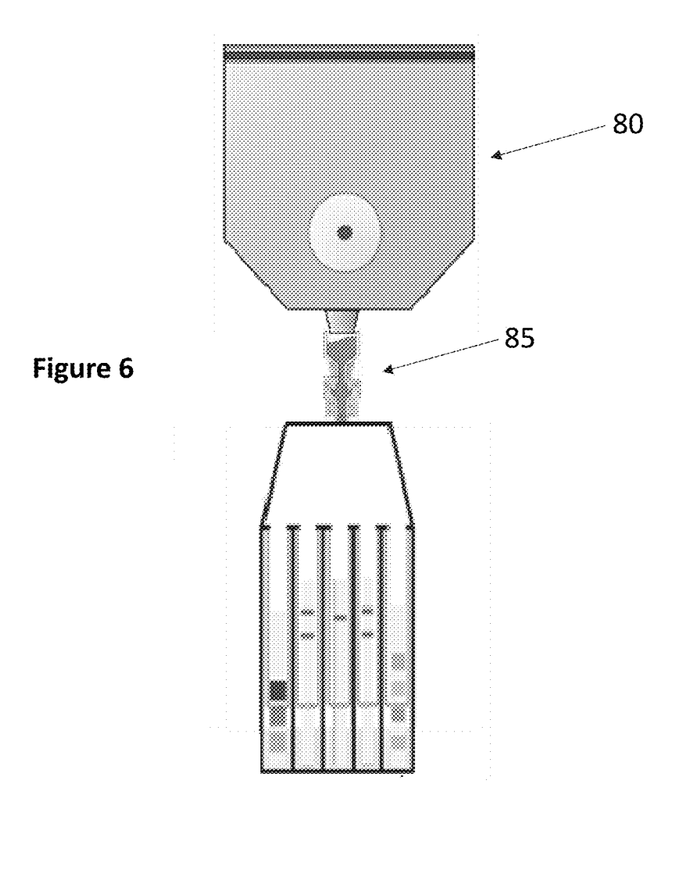
FIG. 6 shows a PDP platform connected to a wide area sample collection device in accordance with one or more embodiments described herein.

An alternative collection modality could include marrying a wide-area surface sampling device, such as a one-handed environmental surface sampling device 80 (e.g., Mano produced by Innovaprep), to the PDP through a port/connector 85 as shown in FIG. 6. The Mano is designed to act as both a biological agent sampling device and transport packaging. It facilitates biological sampling using only one hand while in protective gear. It is capable of sampling both liquid and dry materials from a variety of surfaces such as glass, concrete, stone, wood, and tile, as well as vegetation and soil. By connecting this or a similar wider-area collection device to the PDP by way of a port 85, the sample is collected and immediately tested, plus a larger volume (i.e. 4-5 milliliters) is retained in the Mano for future testing and confirmatory identification.

The PDP embodiments described herein promote compartmentalization and unidirectional sample flow that enables performance of a variety of concurrent detection assays from a single sample. The PDP accommodates both LFI and isothermal DNA amplification assays to provide tiered, orthogonal identification and verification of biothreat agents. Rapid, antigen-specific LFI assays provide yes/no answers within 10 minutes, while a secondary isothermal DNA-amplification step, provided by a COTS recombinase polymerase amplification (RPA) molecular assay, yields an LFI-style "yes/ no" readout in 20 min to 2 hours (temperature dependent). The current design of the PDP supports from 5-10 immuno-based assays (LFIs), but more highly multiplexed versions are possible. The orthogonal, nucleic acid-based identification technologies such as RPA use an LFI-format readout that requires one lane per bioagent-specific assay.

RPA molecular assays are available commercially in a nucleic acid lateral flow (NAFL) assay format for rapid, sensitive, and specific nucleic acid amplification technique detection with an LFI format read-out. The main advantage is that RPA provides eye-readable nucleic acid-based identification without the need for equipment, power, or software. Unlike traditional PCR techniques, RPA does not require sample processing or the traditional series of alternating cycle temperatures to amplify target DNA. Because of this, there is no need for bulky (or proprietary) equipment such as centrifuges, bead beaters, specialized thermo-cycling machines, or assay visualization equipment. It occurs in a single "one pot" reaction space using lyophilized reagents, making it an ideal fit for the PDP platform. As discussed above, the PDP operator agitates the sample in the initial sample compartment using their fingers to help disrupt the cells. After agitation, a clip on the PDP separate the sample compartment from the bladder is opened and the user gently pushes the sample down one or more internal bladder channels leading off from the main compartment, drawing the sample liquid down the assay pouch towards the bottom of the pouch. These bladders feed into individual assay compartments, with one or more holding an individual RPA assay against a unique biological target. Each individual compartment allows only a limited amount of fluid into each assay reaction compartment (fill line) so that each assay occurs in the appropriate reaction volume. Assay results are typically readable within 20 minutes at 37° C. and up to 2 hours at lower temperatures.

The PDP is a new assay form factor designed to provide rapid sample-to-results detection of multiple CBRNE targets in less than an hour. The PDP is a hand-carried, self-contained, inexpensive, simple-to-use, requires minimal sample processing, no external power source, no specialized equipment, no cold chain logistics, and no extra equipment or software. It is customizable to detect multiple agents simultaneously giving it the potential to enhance rapid downrange detection capabilities, lower costs through multiplexing, and significantly reduce reliance of consumables while operating in complex CBRNE environments. The PDP is designed to leverage current COTS and GOTS assay technologies as well as other techniques being developed to deliver eye-readable yes/no detection results of multiple CBRNE targets simultaneously. The PDP can be customized to detect pathogens, toxins and chemicals of interest simultaneously by way of the device's multi-channeled, soft see-through plastic pouch design that consists of inner and outer compartments that promote compartmentalization and/ or unidirectional sample flow. As described above, the design enables the concurrent running of multiple distinct and dissimilar detection assay techniques such as lateral flow immunoassays (LFI), Isothermal molecular assays (i.e., Recombinase Polymerase Amplification, or RPA) and/or paper-based chemical assays (i.e., M8, pH paper, colorimetric) from a single wet or dry sample with minimal sample processing. The PDP seeks to reduce soldier overburden by decreasing size weight (weighs less than 1 ounce), and power (SWaP) as well as training time, electronic burden, while providing a flexible, customizable assay platform that can be rapidly produced, assembled, sustained, and when contaminated, easily to dispose of The embodiments replace the use of traditional assay reaction tubes or plates and provides an inexpensive, multiplex-capable pouch format that is simple to use and easy to carry. The range of detectable threats is only limited by the availability of assays capable of working within the PDP device.

One skilled in the art will readily recognize that the PDP platform may be customized to identify/detect numerous analytes including, but not limited to: chemicals and explosives using, e.g., paper-based chemical detection such as pH, M8, Rosetta papers; bacteria, viruses and toxins using, e.g., paired antigen/antibody and DNA-based detection with high confidence; natural or synthetic narcotics, PBAS including opioids, cannabinoids, tranquilizers, etc.; radiation exposure using, e,g., colorimetric, acute gamma/x-ray does monitoring. In addition to the military applications referenced above, there are numerous other applications which would benefit from the PDP including, but not limited to: food safety and quality from the detection of both chemical and pathogens in food and beverages; plant pathogens, including blight, canker, *Erwinia, Pseudomonas* spp., etc.; insect vectors including vector-borne illnesses such as Lyme disease, malaria, etc. and pen-side livestock testing including cattle, avian, aqua culture, equine, etc.

The invention claimed is:

1. A pocket-sized detection device for detection of one or more analytes, the device comprising:
    a first sample compartment for receiving a sample which may contain the one or more analytes, the first sample compartment including a first sealing component for sealing the first sample compartment once the sample has been received therein;
    a second compartment in fluid connection with the first sample compartment for receiving a fluid sample therefrom, the second compartment containing multiple individual channels;
    a third compartment, including a reservoir, for
        i. loading therethrough individual detectors for placement in the individual channels; and
        ii. receiving at least some of the fluid sample therein from the second compartment, the third compartment including a second sealing component for sealing the third compartment once the individual detectors are loaded in the individual channels;
    wherein, once the first and second sealing components are sealed, the pocket-sized device retains the fluid sample therein; and
    further wherein the multiple individuals channels within the second compartment include micropores at ends thereof for facilitating transfer of at least some of the fluid sample therein to the third compartment.

2. The pocket-sized detection device of claim 1, wherein the individual detectors are selected from the group consisting of assay strips and paper-based chemical detectors.

3. The pocket-sized detection device of claim 1, wherein the device is comprised of one of the following materials selected from the group consisting of a polyethylene low density (LDPE) plastic, a polypropylene film, or a poly nylon plastic, the device including an outer bag and an inner bag, wherein the outer bag is formed of polypropylene having a thickness of 6 mil and the inner bag is formed of polyurethane having a thickness of 2 to 4 mil.

4. The pocket-sized detection device of claim 3, wherein the device weighs less than 1 ounce.

5. The pocket-sized detection device of claim 1, wherein the first sample compartment includes therein lysing beads and the micropores of the individual channels are of a size that does not allow for the lysing beads to pass therethrough.

6. The pocket-sized detection device of claim 1, having an unfolded state and a folded state, wherein in the folded state, the dimensions are 4 inches by 3 inches.

7. The pocket-sized detection device of claim 1, wherein the first sealing component is a zip closure.

8. The pocket-sized detection device of claim 1, wherein the first and second sealing components are adhesive sealing components.

9. The pocket-sized detection device of claim 1, wherein the first sample compartment includes a key card, wherein the key card includes information for comparing to visual result indicators on the individual detectors to determine if the one or more analytes are detected thereby.

10. The pocket-sized detection device of claim 1, further comprising at least one blister pouch located on an inside portion of the first sample compartment, the blister pouch containing a liquid for introducing to a sample in the first sample compartment and mixing therewith to form the fluid sample.

11. The pocket-sized detection device of claim 10, wherein the liquid is a buffer.

12. The pocket-sized detection device of claim 1, wherein the one or more analytes are selected from the group consisting of chemicals, pharmaceutical-based agents, bacteria, virus, toxins and explosives.

13. The pocket-sized detection device of claim 1, further comprising a sample sponge located on an inside portion of the first sample compartment, wherein a user wipes a surface of interest with the sample sponge to collect the sample in the first compartment.

14. The pocket-sized detection device of claim 9, wherein the first sample compartment includes a radiation detector.

* * * * *